(12) United States Patent
Fendrock

(10) Patent No.: US 7,912,536 B2
(45) Date of Patent: Mar. 22, 2011

(54) DISPOSABLE, MULTI-PURPOSE CARDIOVASCULAR AUTONOMIC NEUROPATHY TESTING DEVICE

(75) Inventor: Charles Fendrock, Sudbury, MA (US)

(73) Assignee: NeuroMetrix, Inc., Waltham, MA (US)

( * ) Notice: Subject to any disclaimer, the term of this patent is extended or adjusted under 35 U.S.C. 154(b) by 647 days.

(21) Appl. No.: 11/516,282

(22) Filed: Sep. 6, 2006

(65) Prior Publication Data
US 2007/0066909 A1    Mar. 22, 2007

Related U.S. Application Data

(60) Provisional application No. 60/714,467, filed on Sep. 6, 2005.

(51) Int. Cl.
*A61B 5/0404* (2006.01)
(52) U.S. Cl. ......... 600/513; 600/529; 600/538; 600/484
(58) Field of Classification Search .................. 600/509, 600/513, 529, 532, 537, 538, 484
See application file for complete search history.

(56) References Cited

U.S. PATENT DOCUMENTS

| | | | |
|---|---|---|---|
| 3,680,378 A | 8/1972 | Aurilio et al. | |
| 4,034,743 A | 7/1977 | Greenwood et al. | |
| 4,176,660 A * | 12/1979 | Mylrea et al. | 600/537 |
| 4,813,368 A | 3/1989 | Hutter, III et al. | |
| 5,038,792 A | 8/1991 | Mault | |
| 5,313,943 A | 5/1994 | Houser et al. | |
| 5,549,106 A * | 8/1996 | Gruenke et al. | 600/532 |
| 5,816,246 A | 10/1998 | Mirza | |
| 6,585,662 B1 * | 7/2003 | Jones et al. | 600/538 |
| 2002/0185133 A1 | 12/2002 | Japuntich et al. | |
| 2003/0120169 A1 | 6/2003 | Jones et al. | |
| 2004/0039295 A1 * | 2/2004 | Olbrich et al. | 600/538 |
| 2005/0096558 A1 | 5/2005 | Friedman et al. | |
| 2005/0113703 A1 | 5/2005 | Farringdon et al. | |
| 2005/0160837 A1 | 7/2005 | Tellenbach et al. | |

* cited by examiner

*Primary Examiner* — Scott M Getzow
*Assistant Examiner* — Joseph M Dietrich
(74) *Attorney, Agent, or Firm* — Pandiscio & Pandiscio

(57) ABSTRACT

A disposable, multi-purpose cardiovascular autonomic neuropathy testing device which comprises a tubular body having a distal end, a proximal end and a passageway extending therebetween; at least one ECG electrode disposed on the exterior surface of the tubular body for monitoring ECG signals of a patient holding the tubular body; a breathing sensor attached to the tubular body for monitoring breathing through the passageway; a closure mechanism attached to the tubular body for selectively restricting the passageway; and a pressure monitor attached to the tubular body for confirming when a pre-determined pressure has been established in the passageway; whereby the testing device can be used to conduct (i) metronomic breathing tests, (ii) Valsalva maneuver tests, and (iii) HRV standing tests.

37 Claims, 9 Drawing Sheets

DISPOSABLE, MULTI-PURPOSE CARDIOVASCULAR AUTONOMIC NEUROPATHY TESTING DEVICE

REFERENCE TO PENDING PRIOR PATENT APPLICATION

This patent application claims benefit of pending prior U.S. Provisional Patent Application Ser. No. 60/714,467, filed Sep. 6, 2005 by Charles Fendrock for MULTIPURPOSE, DISPOSABLE, CARDIOVASCULAR AUTONOMIC NEUROPATHY TESTING SENSOR, which patent application is hereby incorporated herein by reference.

FIELD OF THE INVENTION

This invention relates to devices for testing cardiovascular autonomic neuropathy in general, and more particularly to a disposable testing device capable of performing a plurality of standard tests for diagnosing cardiovascular autonomic neuropathy.

BACKGROUND OF THE INVENTION

Cardiovascular autonomic neuropathy is typically caused by metabolic, toxic and/or genetic damage to autonomic nerve fibers, and/or by metabolic, toxic and/or genetic damage to small diameter nerve fibers. Cardiovascular autonomic neuropathy is common, for example, in individuals with diabetes. Prevalence estimates vary, but it is probable that at least 25% of the diabetes population suffers from cardiovascular autonomic neuropathy.

There are many clinical manifestations of cardiovascular autonomic neuropathy including, but not limited to, resting tachycardia, exercise intolerance and orthostatic hypotension.

Cardiovascular autonomic neuropathy is often associated with silent myocardial ischemia (i.e., a "silent heart attack"), and is also associated with high rates of sudden death.

Additionally, with cardiovascular autonomic neuropathy, damage to nerves in the cardiovascular system can interfere with the body's ability to adjust blood pressure and heart rate. As a result, blood pressure may drop sharply after sitting or standing, causing a person to feel light-headed or even to faint. Damage to the nerves that control heart rate can mean that the heart rate stays high, instead of rising and falling in response to normal body functions and exercise. All of these effects can be detrimental to the patient's health.

There are several standard medical tests which are performed to help diagnose cardiovascular autonomic neuropathy. These tests generally require that the patient perform different specific physical exercises while the patient's electrocardiogram (ECG) is monitored. In particular, changes in the patient's heart rate (from one beat to the next) are traditionally observed before, during and after the test, depending on the specific test being performed. More specifically, the time interval between the peaks in two sequential "R" waves in the ECG waveform—sometimes called the "R-R" interval, and also commonly known as beat-to-beat "heart rate variability" (HRV)—is monitored and analyzed.

The most common tests performed to diagnose cardiovascular autonomic neuropathy are as follow:

1. Testing HRV In Response To Metronomic Or Paced Breathing At 6 Times Per Minute ("Metronomic Breathing Tests"). With the patient at rest and supine, the patient breathes at a rate of 6 breaths/minute while the heart rate is monitored by an ECG device. A difference in heart rate between inspiration and expiration of >15 beats/minute is considered normal, and a difference in heart rate between inspiration and expiration of <10 beats/minute is considered abnormal.
2. Testing HRV In Response To The Valsalva Maneuver ("Valsalva Manuever Tests"). The patient forcibly exhales into a mouthpiece while an associated manometer measures pressure. The patient exhales hard enough to increase the exhalation pressure to approximately 40 mm Hg for 15 seconds while the ECG is monitored. Often this test is conducted in a simpler manner, by simply having the patient attempt to exhale through the mouth while the mouth is closed so as to create a high backpressure condition, but this closed-mouth approach is generally not preferred since it tends to suffer from inconsistent repeatability. Healthy patients develop tachycardia during strain, and an overshoot bradycardia upon release. The ratio of longest R-R to shortest R-R should generally be >1.2 in healthy patients.
3. Testing HRV In Response To Standing ("HRV Standing Tests"). During continuous ECG monitoring, the patient's R-R interval is measured at beats 15 and 30 after standing. Normally, a tachycardia is followed by reflex bradycardia (i.e., an abnormally slow heartbeat, usually less than 60 beats per minute). The 30:15 ratio is normally >1.03 in healthy patients.

Many systems are available to perform cardiovascular autonomic neuropathy testing. However, most of these systems are essentially just conventional ECG machines adapted for simple HRV analysis. More particularly, with these systems, the skin of the patient is prepared for the application of 3 or more individual ECG electrodes. These electrodes are generally applied to the shoulders and/or chest of the patient, and possibly to one or both legs of the patient, thus requiring that the patient at least partially disrobe. The ECG electrodes are then connected with wires to the system's ECG monitor.

Detection of the patient's breathing is generally conducted using a permanent, and relatively expensive, airflow pressure transducer, to which a disposable mouthpiece is attached. While generally effective, this arrangement constitutes a relatively expensive solution to the problem of monitoring metronomic breathing. The use of a permanent airflow pressure transducer also raises the possibility of cross-contamination by infectious agents, since the transducer is reused from patient to patient.

The Ansar ANS-R1000 system (The Ansar Group, Inc. of Philadelphia, Pa.) is one such cardiovascular autonomic neuropathic testing product that is currently commercially available. The Anscore Health Management System (Boston Medical Technologies, Inc. of Wakefield, Mass.) was another (the company is no longer in business). However, the Ansar ANS-R1000 system and the Anscore Health Management System are/were complex systems, requiring highly trained operators and requiring significant preparation of the patient due to the need to apply the ECG electrodes to the patient (and the associated patient disrobing). These systems, and others like them, are not believed to constitute a readily-available, cost-effective and/or practical in-office, rapid-diagnostic tool for application to the primary care physician and/or small clinic markets.

The complexity, inconvenience, and required time and expense associated with currently-available cardiovascular autonomic neuropathy testing systems all act to inhibit wider adoption of these systems. This is a serious issue in view of, for example, the rapidly growing incidence of Type 1 and Type 2 diabetes, which makes this type of testing increasingly important for diagnosing the cardiovascular autonomic neuropathy linked to these types of diabetes.

Thus, a disposable, multi-purpose cardiovascular autonomic neuropathy testing device would be a key enabling component in a new, low-cost, small form-factor, battery-powered, dedicated cardiovascular autonomic neuropathy testing system.

It is, therefore, a principal object of the present invention to provide a disposable, multi-purpose testing device which can be used to quickly and easily test for cardiovascular autonomic neuropathy.

SUMMARY OF THE INVENTION

The present invention comprises the provision and use of a novel disposable, multi-purpose cardiovascular autonomic neuropathy testing device which comprises:

a tubular body having a distal end, a proximal end and a passageway extending therebetween;

at least one ECG electrode disposed on the exterior surface of the tubular body for monitoring ECG signals of a patient holding the tubular body;

a breathing sensor attached to the tubular body for monitoring breathing through the passageway;

a closure mechanism attached to the tubular body for selectively restricting the passageway; and a pressure monitor attached to the tubular body for confirming when a pre-determined pressure has been established in the passageway;

whereby (i) when the closure mechanism is in a first configuration such that the passageway is unrestricted, the testing device can be used to conduct metronomic breathing tests by having the patient breath through the passageway while the patient's ECG is monitored by the at least one ECG electrode, (ii) when the closure mechanism is in a second configuration such that the passageway is restricted, the testing device can be used to conduct Valsalva maneuver tests by having the patient breath into the passageway until the pressure monitor confirms that the pre-determined pressure has been established within the passageway while the patient's ECG is monitored by the at least one ECG electrode, and (iii) when the closure mechanism is in either the first configuration or the second configuration, the testing device can be used to conduct HRV standing tests by having the patient stand and having the patient's ECG monitored by the at least one ECG electrode.

In a preferred form of the present invention, the disposable, multi-purpose cardiovascular autonomic neuropathy testing device can be fabricated using the simple and inexpensive manufacturing techniques commonly used in manufacturing electrodes for monitoring the electrical activity of body functions (e.g., EKG electrodes, neurological electrodes, defibrillator electrodes, etc.).

It will be appreciated that the novel testing device includes everything required to perform multiple standard cardiovascular autonomic neuropathy tests in a single, integrated and easily disposable package, i.e., a body, ECG electrodes, a breathing sensor, a closure mechanism and a pressure monitor, whereby the testing device can be used for metronomic breathing tests, Valsalva maneuver tests, and HRV standing tests.

BRIEF DESCRIPTION OF THE DRAWINGS

These and other objects and features of the present invention will be more fully disclosed or rendered obvious by the following detailed description of the preferred embodiments of the invention, which should be read in conjunction with the accompanying drawings wherein.

DETAILED DESCRIPTION OF THE PREFERRED EMBODIMENTS

The Novel Testing Device in General

Figure 1:
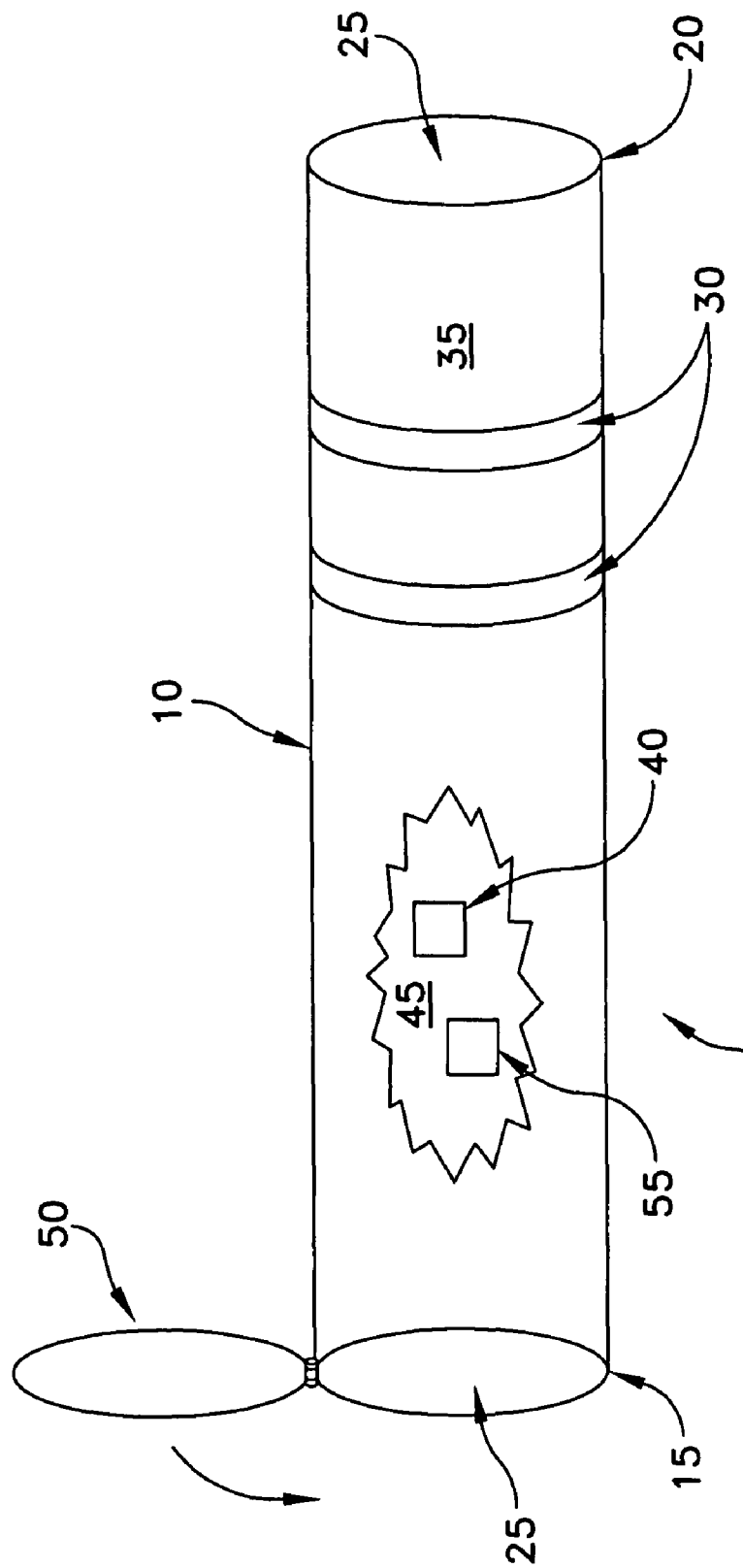
FIG. 1 is a schematic view of a novel testing device formed in accordance with the present invention.

Looking first at FIG. 1, the present invention comprises the provision and use of a novel disposable, multi-purpose cardiovascular autonomic neuropathy testing device 5.

Testing device 5 comprises a tubular body 10 having a distal end 15, a proximal end 20 and a passageway 25 extending therebetween.

At least one ECG electrode 30 is disposed on the exterior surface 35 of tubular body 10. The at least one ECG electrode 30 is used for monitoring the ECG signals of a patient holding tubular body 10. To this end, the at least one ECG electrode 30 is positioned on tubular body 10 for easy contact by the fingers of the patient, whereby to pick up the ECG signals of the patient. This construction eliminates the need for the patient to disrobe so that ECG electrodes may be applied the shoulders or chest of the patient.

A breathing sensor 40 is attached to tubular body 10 for monitoring breathing through passageway 25. Breathing sensor 40 is preferably disposed on the interior surface 45 of tubular body 10. Breathing sensor 40 may comprise any sensor capable of detecting airflow through passageway 25.

Thus, breathing sensor 40 may comprise a mechanically-based flow sensor. By way of example but not limitation, such a mechanically-based flow sensor may comprise a strain-type of device which, when mounted in the air flow in a cantilevered arrangement, bends under air flow, thus changing the value of the strain element, which can be detected and used as a measure of air flow.

Alternatively, and more preferably, breathing sensor 40 comprises a thermally-based sensor which, by detecting the changes in temperature between relatively warm exhaled breath and relatively cool inhaled air, can detect breathing. By way of example but not limitation, such a thermally-based sensor may comprise positive temperature coefficient thermistors, negative temperature coefficient thermistors, and semiconductor-based temperature sensing elements.

A closure mechanism 50 is attached to tubular body 10 for selectively restricting passageway 25. Closure mechanism 50 is preferably disposed on distal end 15 of tubular body 10. Closure mechanism 50 may comprise any mechanism capable of restricting passageway 50, whereby to create a pressure chamber within tubular body 10 for use in performing Valsalva maneuver testing. By way of example but not limitation, closure mechanism 50 may comprise a simple flip-cap closure such as is shown in FIG. 1. However, numerous other types of closure mechanisms will be apparent to those skilled in the art in view of the present disclosure.

Figure 7:
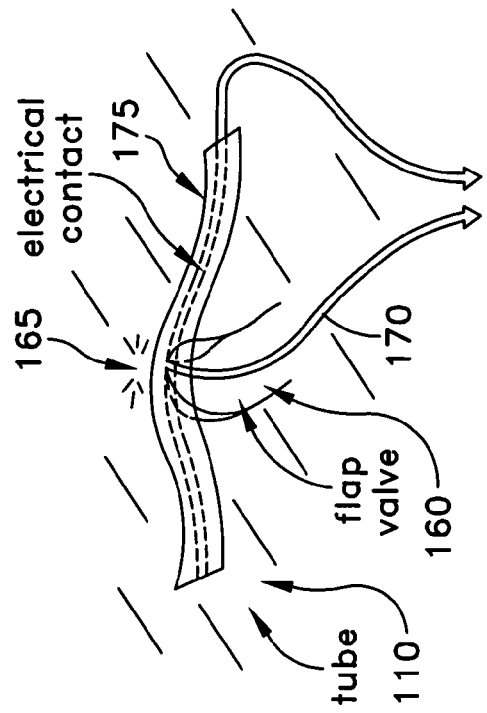
FIGS. 6 and 7 are schematic views showing construction details of one preferred form of pressure monitor for confirming when a pre-determined pressure has been established in the passageway, wherein the pressure monitor comprises a flap valve and detection switch.
Figure 6:
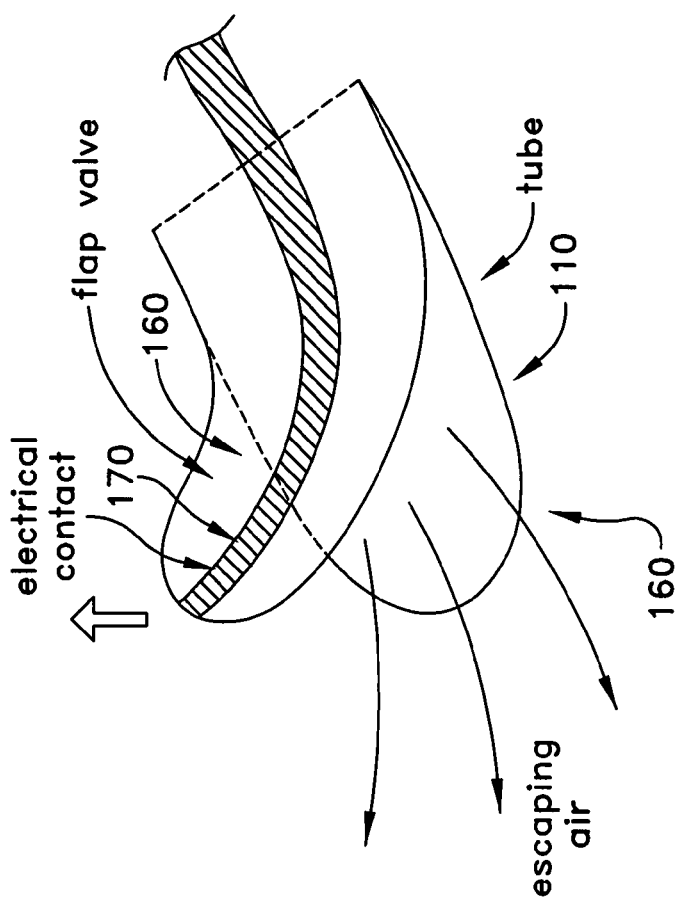
Figure 8:
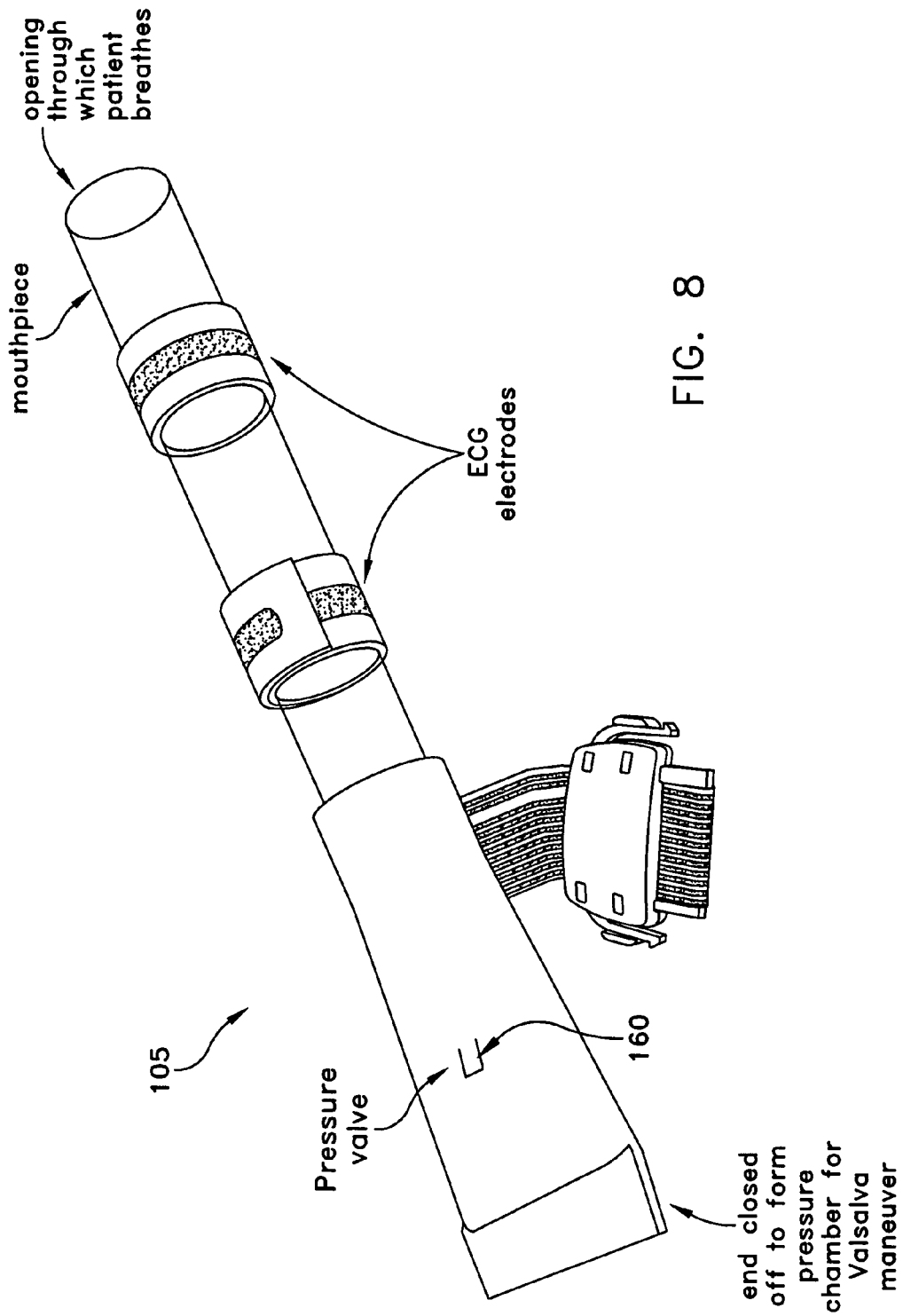
FIG. 8 is a schematic view of the testing device shown in FIG. 2, except that the testing device has been altered by the user so as to close off the distal end of the testing device, whereby to create a pressure chamber for use in performing Valsalva maneuver testing.

A pressure monitor 55 is attached to tubular body 10 for confirming when a pre-determined pressure has been established in passageway 25. Pressure monitor 55 is preferably disposed on the interior surface 45 of tubular body 10. By way of example but not limitation, pressure monitor 55 may comprise the self-regulating flap valve and detection switch shown in FIGS. 6 and 7. However, pressure monitor 55 may also comprise other constructions such as a strain-sensitive printed resistive (or other type) element that constitutes part of the body construction, which deforms under pressure in the Valsalva maneuver mode and that can be detected, or a pressure valve that is formed (e.g., molded) as part of the mouthpiece, or a sound-creation element which requires enough air pressure with slight air flow to make a distinctive audible noise as a means to indicate that the pre-determined pressure has been reached and that can be made as part of the mouthpiece or added as a separate part, etc. Still other types of pressure monitors will be apparent to those skilled in the art in view of the present disclosure. Furthermore, depending on the particular construction chosen for pressure monitor 55, with some of the constructions, the pressure monitor can be automatically monitored electronically, and thus able to be recorded. With other constructions of the pressure monitor, the construction may be more of an "open loop" construction, in that the loop is closed and verification of pressure having been reached is by the patient or by attending medical personnel.

Testing device 5 also comprises various electrical connectors (not shown) of the sort well known in the art for connecting its electrical components (e.g., ECG electrodes 30, breathing sensor 40, pressure monitor 55, etc.) to "off-device" electrical units (e.g., associated signal monitoring electronics).

Testing device 5 may be used to conduct a plurality of cardiovascular autonomic neuropathy tests. More particularly, testing device 5 may be used to conduct metronomic breathing tests, Valsalva maneuver tests and HRV standing tests.

When testing device 5 is to be used to conduct metronomic breathing tests, closure mechanism 50 is placed in a first configuration such that passageway 25 is unrestricted. The patient then breathes through passageway 25 while the patient's inspiration and expiration is monitored by breathing sensor 40 and the patient's ECG is monitored by the at least one ECG electrode 30.

When testing device 5 is to be used to conduct Valsalva maneuver tests, closure mechanism 50 is placed in a second configuration such that passageway 25 is restricted. The patient then breathes into passageway 25 until pressure monitor 55 confirms that a pre-determined pressure has been established in passageway 25 while the patient's ECG is monitored by at least one ECG electrode 30.

When testing device 5 is to be used to conduct HRV standing tests, the patient stands and the patient's ECG is monitored by the at least one ECG electrode 30.

Novel Testing Device Comprising a Rolled Substrate with a Molded Mouthpiece

In a preferred form of the present invention, the disposable, multi-purpose cardiovascular autonomic neuropathy testing device 5 can be fabricated (in whole or in part) using the simple and inexpensive manufacturing techniques commonly used in manufacturing electrodes for monitoring the electrical activity of body functions (e.g., EKG electrodes, neurological electrodes, defibrillator electrodes, etc.).

Referring next to FIGS. 2-8, there is shown a disposable, multi-purpose cardiovascular autonomic neuropathy testing device 105 which comprises one preferred form of the present invention. Testing device 105 generally comprises a rolled substrate 110 and a molded mouthpiece 115. Rolled substrate 110 and molded mouth piece 115 together form the hollow tubular body of testing device 105.

Substrate 110 is preferably formed from a clear or colored plastic (e.g., MYLAR®), preferably in the range of 0.002 inches to 0.007 inches thick, depending on the desired stiffness. In general, it is preferred that substrate 110 be flexible enough to be rolled up from a flat sheet configuration (FIGS. 3-5) to a tubular configuration (FIG. 2), but rigid enough to provide body when the substrate is in its rolled configuration.

A conductive pattern is deposited (e.g., by silk screening, chemical plating or other conventional means well known to those skilled in the art) on the substrate so as to form (i) a plurality of ECG electrodes 120 for picking up ECG signals from the patient, and (ii) electrical traces 125 for connecting ECG electrodes 120 to a connector 130 for connecting testing device 105 to associated signal monitoring electronics (not shown). Electrical traces 125 also connect a thermistor 135 (which functions as an air flow sensor, whereby to provide breathing sensing, as will hereinafter be discussed) and an electronic serial number memory component 140 to connector 130. Electronic serial number memory component 140 is mounted to substrate 110 and may be encoded with a unique serial number. Electronic serial number memory component 140 may also be encoded to reflect other device characteristics, both fixed (e.g., device size, model type, etc.) and real-time (e.g., that the testing device has been previously used). Graphical and textual information such as instructions (not shown) may also be printed on substrate 110.

The ECG electrode areas 120 are positioned on testing device 105 so that they will contact the fingers of a patient holding testing device 5, whereby to acquire the ECG signals needed for testing. A conductive gel layer 143 is silk-screened or otherwise dispensed over the electrode areas. During use, conductive gel layer 143 facilitates acquisition of the ECG signal from the patient's fingertips. A protective release liner 144 is applied over the gel areas.

Thermistor 135 (i.e., the breathing sensor) and electronic serial number memory component 140 are attached to the electrical traces 125 on substrate 110 with conductive epoxy, a process well known to those skilled in the art. Thermistor 135 is a commonly-available electronic component whose electrical resistance changes with temperature. As a result, when the patient breathes during the metronomic breathing test, the resistance of thermistor 135 rises and falls with inspiration (cool air in) and expiration (hot air out). This change in resistance is easily measured, thereby providing an indication of the patient's breathing, and can provide a record (via electrical traces 125 and connector 130) showing that this portion of the test has been conducted and indicating the results. The electronic serial number memory component 140 is also a readily-available programmable electronic component that is well known to those skilled in the art.

Figure 2:
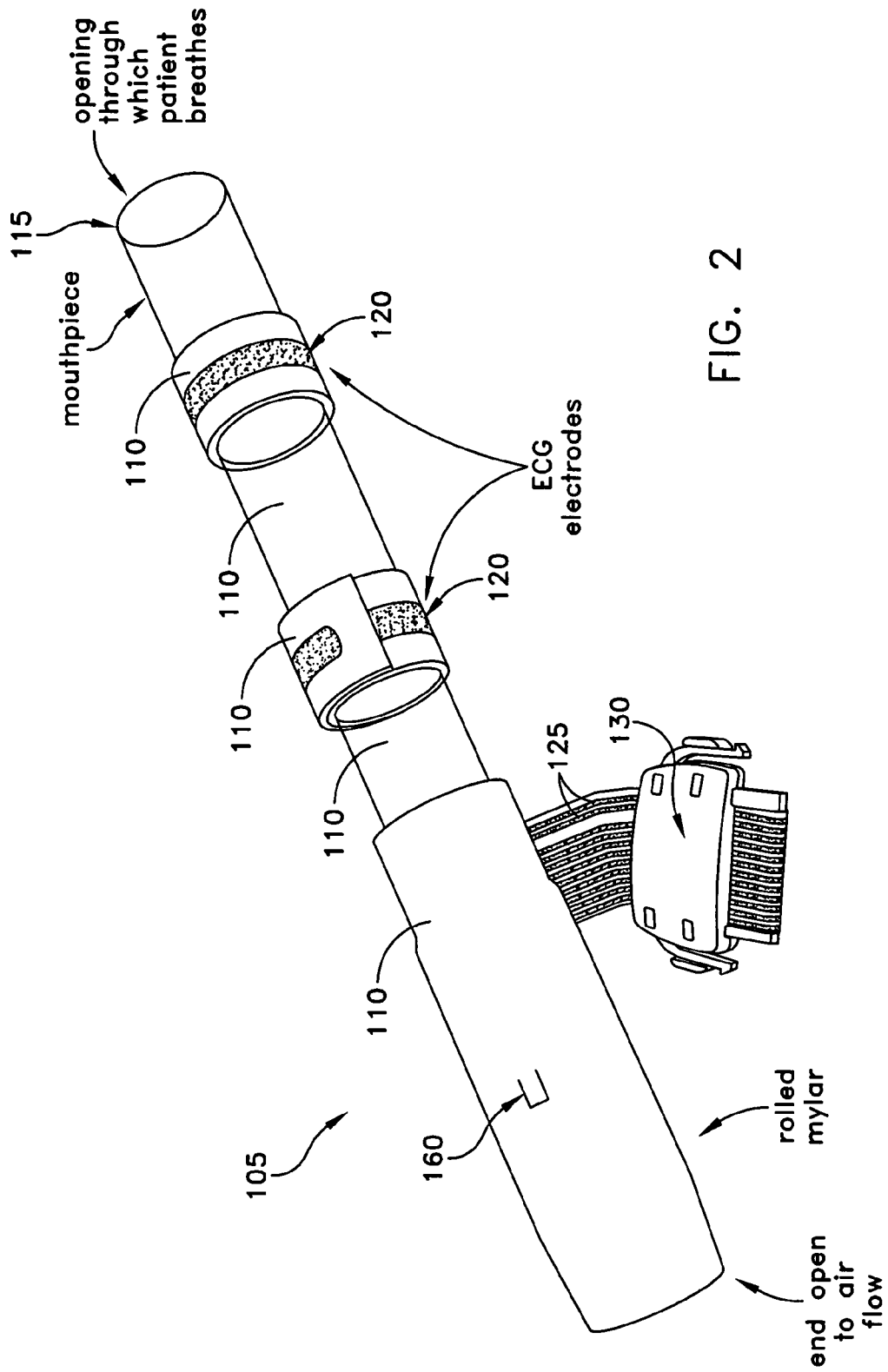
FIG. 2 is a schematic view of another novel testing device formed in accordance with the present invention, in which the body of the testing device comprises a rolled substrate and a molded mouthpiece, wherein the rolled substrate is mounted to the molded mouthpiece so that they together form the overall structure of the testing device, and wherein the testing device has (i) a passageway through which the patient can breathe, (ii) a plurality of ECG electrodes disposed along the mouthpiece to acquire ECG signals from the patient when the testing device is being held (and the ECG electrodes electrically contacted) by the patient, and (iii) a thermistor (not seen in FIG. 2) mounted on the inside of the passageway which is used to detect the breathing of the patient.
Figure 3:
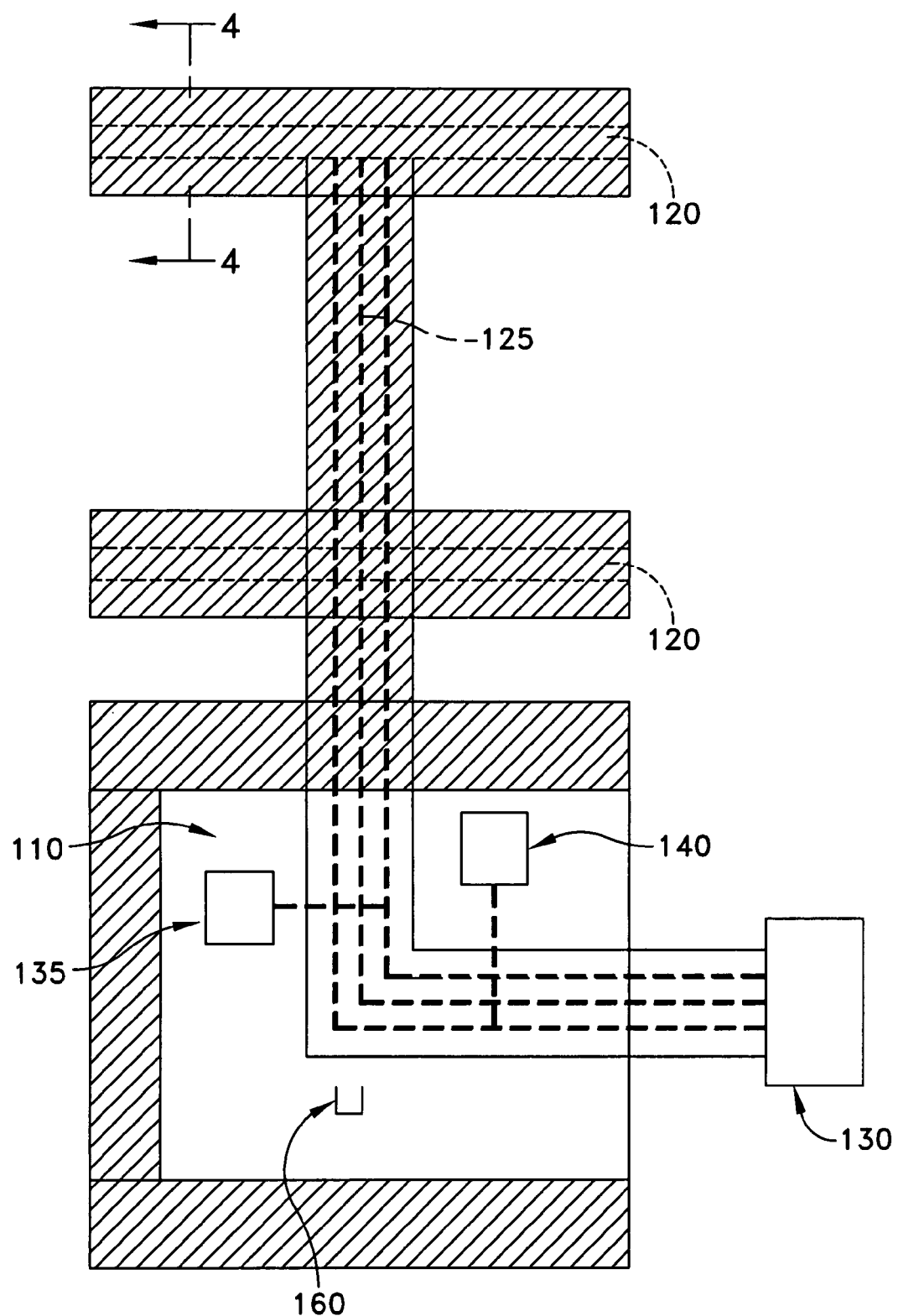
FIG. 3 is a schematic view showing the interior side of the substrate, with the substrate being shown separated from the molded mouthpiece and in an unrolled condition.
Figure 4:
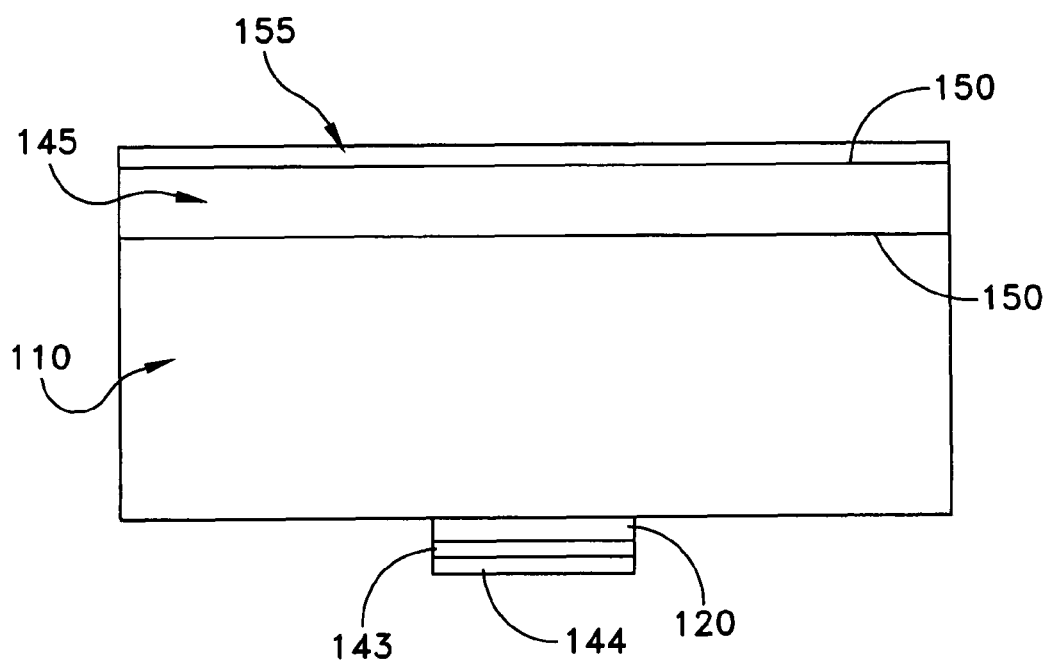
FIG. 4 is a sectional view taken along line 4-4 of FIG. 3.
Figure 5:
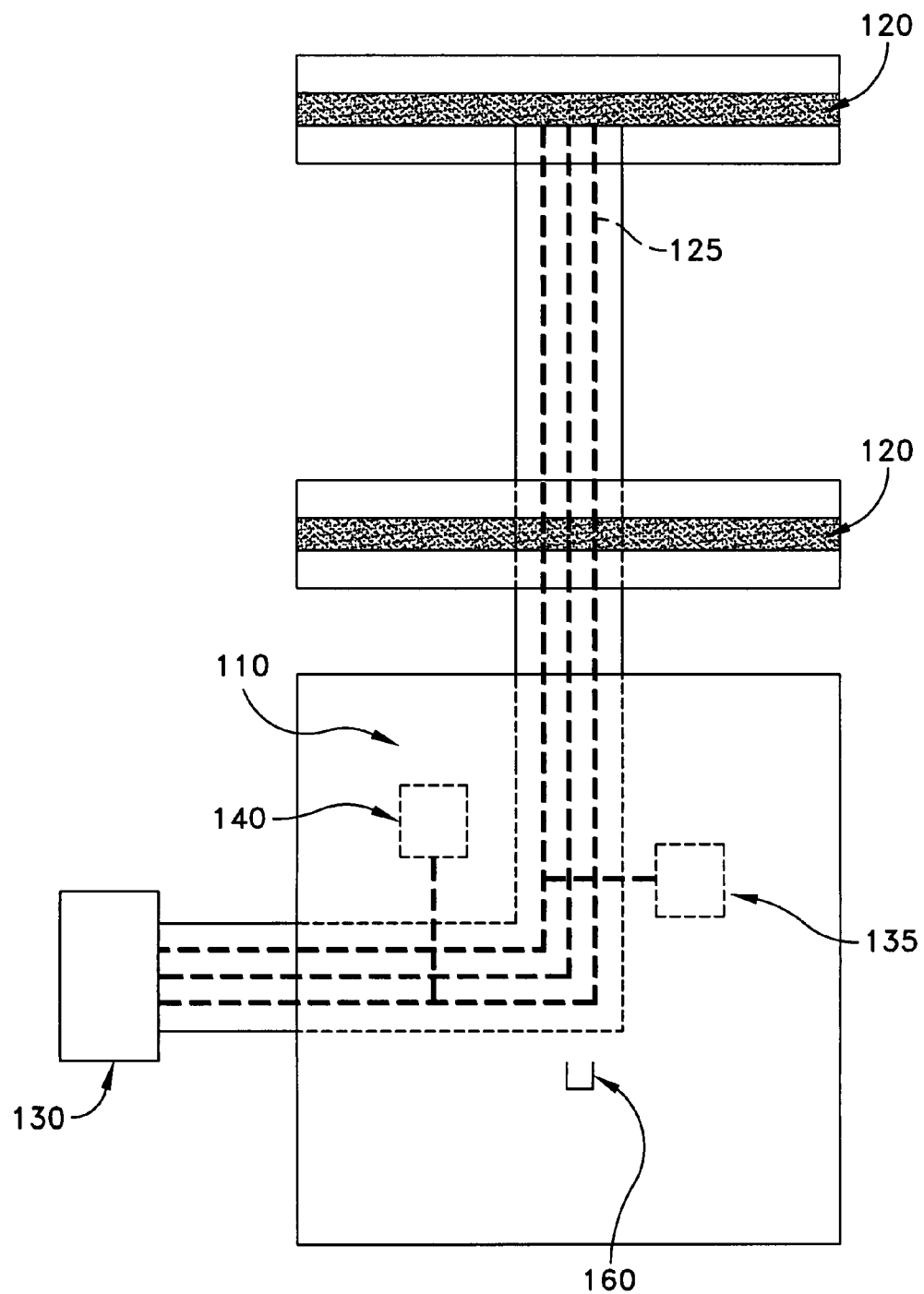
FIG. 5 is a schematic view showing the exterior side of the substrate, with the substrate being shown separated from the molded mouthpiece and in an unrolled condition.

A layer of polyethylene foam 145, typically in the range of 0.030 to 0.060 inches in thickness, with adhesive 150 applied to one or both sides, and with a release liner 155 covering the adhesive, is selectively die-cut or laser-cut to the desired shape (i.e., to match the shape of selected portions of substrate 110), and selectively kiss-cut to create peel-away areas for later construction steps and for when the testing device is in actual use. The layer of polyethylene foam 145 is then selectively laminated to substrate 110, as shown in FIGS. 3 and 4. The adhesive-covered polyethylene foam 145, 155 permits substrate 110 to be, during construction, (i) initially tangentially secured to molded mouthpiece 115, and (ii) thereafter rolled into a cylindrical configuration and secured in this position, so as to form, together with molded mouthpiece 115, the overall body of testing device 105 (FIG. 2).

In order to form a closure mechanism for testing device 105, the distal end of the rolled substrate 110 may be configured so that its distal end can be selectively closed off and held in this closed-off position, i.e., when the testing device is to be used for the Valsalvic maneuver testing. More particularly, and looking now at FIGS. 3 and 8, a kiss-cut release liner, disposed within the perimeter of the distal opening in the rolled substrate, is removed, exposing an adhesive layer, and then the end of the tube is sealed closed with the fingers, thus forming the pressure chamber used for the Valsalva maneuver.

Looking next at FIGS. 2, 3 and 5-8, there is shown a flap valve and detection switch construction which is used as the pressure monitor during Valsalva maneuver testing. More particularly, a tab or other shape is cut by laser or with a punch so as to create a pressure-controlled flap valve to regulate the pressure to 40 mm Hg, or any other desired pressure, depending on the size and shape of the tab, and the thickness and type of the substrate material. As the flap rises with increasing pressure, a conductive trace on the free end of the flap contacts a counterpart conductive trace on a bridge that is positioned over the flap, whereby to complete the circuit and thereby detect and indicate that the correct pressure has been reached and maintained for the duration of the Valsalva maneuver testing. More particularly, and still looking at FIGS. 2, 3 and 5-8, there is shown a pressure valve 160 (e.g., a flap valve) which is formed in substrate 110 by punching or laser cutting. A "valve open" detector switch 165 (comprising a first electrical contact 170 and a second electrical contact 175) is constructed about pressure valve 160, by adhering a first electrical contact 170 to pressure valve 160 with a conductive adhesive, and by adhering a second electrical contact 175 to substrate 110 with conductive adhesive. When a target pressure is established within the interior of the testing device's tubular body, the two electrical contacts 170, 175 will engage one another so as to complete an electrical circuit. This construction provides an indication that a pre-determined pressure (e.g., approximately 40 mm Hg of pressure) has been achieved and sustained during Valsalva maneuver testing.

The flap valve can also comprises a simple visual indicator, without the overhead bridge electrical contact, that the patient simply observes as having risen in height when sufficient airflow and pressure have been achieved by exhaling into the disposable.

Molded mouthpiece 115 is separately manufactured as a molded or fabricated part, a process well known to those skilled in the art. During assembly, selectively die-cut and kiss-cut areas of adhesive-covered polyethylene foam 145, 155 are utilized to mount substrate 110 to molded mouthpiece 115. More particularly, adhesive areas are exposed, substrate 110 is initially tangentially secured to molded mouthpiece 115, and then substrate 110 is rolled into a tubular configuration and secured in this position (e.g., substrate 110 is mounted onto the rigid mouthpiece and sealed along the seam) so as to create a permanently cylindrical shape such as is shown in FIG. 2.

The serial number and other information as desired is programmed into the electronic serial number memory component 140, and the assembly is finalized after being sealed into a moisture barrier pouch.

Thus, with testing device 105, the tubular body is provided by rolled substrate 110 and molded mouthpiece 115; the at least one ECG electrode is provided by ECG electrodes 120; the breathing sensor is provided by thermistor 135; the closure mechanism is provided by the deformable rolled substrate and the adhesive-covered polyethylene foam 145, 155; and the pressure monitor is provided by flap valve 160.

Testing device 105 may be used to conduct a plurality of cardiovascular autonomic neuropathy tests. More particularly, testing device 105 may be used to conduct metronomic breathing tests, Valsalva maneuver tests and HRV standing tests.

When testing device 105 is to be used to conduct metronomic breathing tests, the device's passageway is kept unrestricted. The patient then breathes through the passageway while the patient's inspiration and expiration is monitored by thermistor 135 and the patient's ECG is monitored by the at least one ECG electrodes 120.

When testing device 105 is to be used to conduct Valsalva maneuver tests, the device's passageway is restricted by collapsing the distal end of the tube and securing it in the collapsed condition using the adhesive-covered polyethylene foam 145, 155. The patient then breathes into the passageway until flap valve 160 confirms that a pre-determined pressure has been established in the passageway while the patient's ECG is monitored by the ECG electrodes 120.

When testing device 105 is to be used to conduct HRV standing tests, the patient stands and the patient's ECG is monitored by the ECG electrodes 120.

Novel Testing Device Comprising a Rolled Substrate without a Molded Mouthpiece

Figure 9:
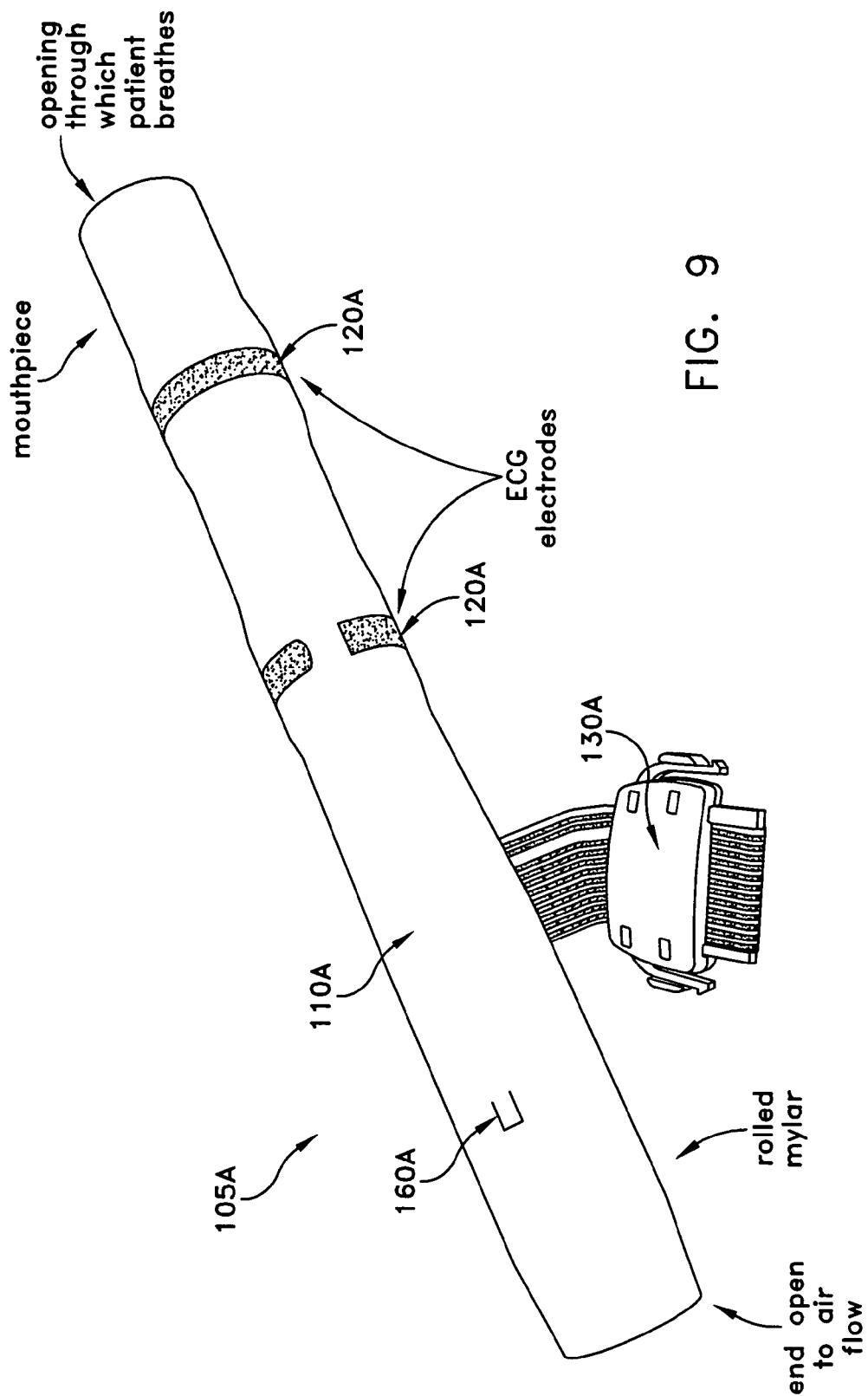
FIG. 9 is a schematic view showing another novel testing device formed in accordance with the present invention, wherein the entire tubular body of the testing device is formed by the rolled substrate and the molded mouthpiece is omitted.

Another novel testing device 105A is shown in FIG. 9. Testing device 105A is similar to testing device 105 except as will hereinafter be discussed. More particularly, in the construction shown in FIG. 9, the separate molded mouthpiece 115 is omitted and, instead, the mouthpiece portion of the testing device is provided by an extension of the rolled substrate through which the patient would breathe. This construction, while typically being less rigid than a construction using a molded mouthpiece, has the advantage of being lower in cost, both because of eliminating the separate molded mouthpiece and because of eliminating the labor to assemble the substrate to the molded mouthpiece. The construction sequence is generally similar that of the testing device 105 shown in FIG. 2, except that substrate 110A is not mounted to a mouthpiece 115 before being rolled into its tubular configuration.

Novel Testing Device Comprising a Molded Body with Substrate Overlay

Figure 10:
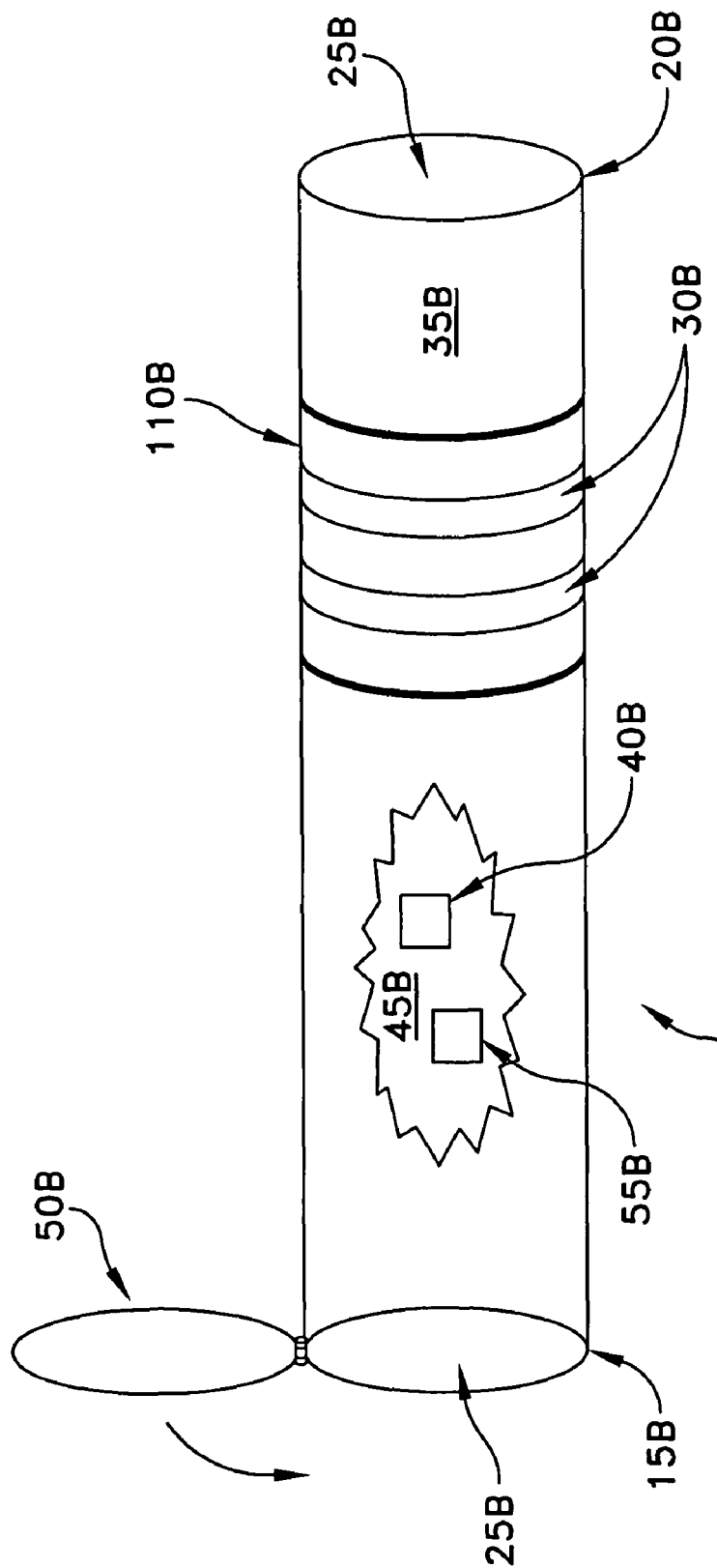
FIG. 10 is a schematic view showing another novel testing device formed in accordance with the present invention.

Another testing device 5B is shown in FIG. 10. Testing device 5B is similar to testing device 5 disclosed above except as will hereinafter be discussed. More particularly, in the construction shown in FIG. 10, body 5B is formed out of a singular (e.g., molded) construction. A substrate 110B is applied to the exterior 35B of body 5B. Substrate 110B is similar to the substrate 110 disclosed above, except that it may omit thermistor 135, since breathing sensor 40B is provided on body 5B. Substrate 110B includes ECG electrodes 30B and the adhesive-covered polyethylene foam construction permitting the substrate to be mounted to body 5B.

MODIFICATIONS

While the foregoing invention has been described with reference to its preferred embodiments, various alterations and modifications will occur to those skilled in the art in view of the present disclosure. All such alterations and modifications are considered to fall within the scope of the invention.

What is claimed is:

1. A disposable, multi-purpose cardiovascular autonomic neuropathy testing device which comprises:
   a tubular body having a distal end, a proximal end, and a single passageway defined thereby and extending therethrough;
   at least one ECG electrode disposed on an exterior surface of said tubular body for sensing ECG signals of a patient holding said tubular body;
   a breathing sensor attached to an interior surface of said tubular body for measuring air flow caused by breathing through the passageway;
   a closure mechanism attached to the distal end of said tubular body for selectively restricting the passageway, said closure mechanism having a first configuration in which the passageway is unrestricted, and a second configuration in which the passageway is selectively restricted; and
   a pressure monitor attached to the interior surface of said tubular body for confirming when a pre-determined pressure has been established in the passageway;
   whereby when said closure mechanism is in the first configuration such that the passageway is unrestricted, the testing device is adapted for conducting metronomic breathing tests wherein the patient breathes through the passageway while the patient's ECG is monitored by said at least one ECG electrode, and
   the testing device is further adapted for conducting HRV standing tests wherein the patient's ECG is monitored by the ECG electrode;
   whereby when the closure mechanism is in the second configuration such that the passageway is restricted, the testing device is adapted to conduct Valsalva maneuver tests wherein the patient breathes into the passageway until said pressure monitor confirms that the pre-determined pressure has been established in the passageway while the patient's ECG is monitored by said at least one ECG electrode.

2. A testing device according to claim 1 wherein said tubular body comprises a rolled-substrate.

3. A testing device according to claim 2 wherein said tubular body further comprises a molded mouthpiece.

4. A testing device according to claim 2 wherein said rolled substrate is formed of a plastic.

5. A testing device according to claim 4 wherein said rolled substrate is 0.002 inches to 0.007 inches thick.

6. A testing device according to claim 2 wherein said rolled substrate is sufficiently flexible to be rolled from a flat sheet configuration, but sufficiently rigid to provide body when said rolled substrate is in a rolled configuration.

7. A testing device according to claim 2 wherein the testing device further comprises a conductive pattern disposed on the rolled substrate so as to form (i) said at least one ECG electrode, and (ii) a plurality of electrical traces.

8. A testing device according to claim 1 wherein said tubular body comprises a molded element.

9. A testing device according to claim 8 wherein said molded element is provided with a substrate secured thereto.

10. A testing device according to claim 9 wherein the substrate is provided with a conductive pattern deposited on the substrate so as to form (i) said at least one ECG electrode, and (ii) a plurality of electrical traces.

11. A testing device according to claim 1 wherein a substrate is secured to said tubular body, and the substrate forms a conductive pattern on the substrate so as to form (i) said at least one ECG electrode, and (ii) a plurality of electrical traces.

12. A testing device according to claim 1 wherein a conductive pattern is disposed on said tubular body so as to form (i) said at least one ECG electrode, and (ii) a plurality of electrical traces.

13. A testing device according to claim 1 wherein said breathing sensor is disposed in an interior of said tubular body.

14. A testing device according to claim 1 wherein said breathing sensor comprises a mechanically-based flow sensor.

15. A testing device according to claim 14 wherein said mechanically-based flow sensor comprises a strain-type device.

16. A testing device according to claim 1 wherein said breathing sensor comprises a thermally-based sensor.

17. A testing device according to claim 16 wherein said thermally-based sensor comprises a thermistor.

18. A testing device according to claim 17 wherein said thermistor comprises a positive temperature coefficient thermistor.

19. A testing device according to claim 17 wherein said thermistor comprises a negative temperature coefficient thermistor.

20. A testing device according to claim 16 wherein said thermally-based sensor comprises a semiconductor-based temperature sensing element.

21. A testing device according to claim 1 wherein said closure mechanism comprises a flip-cap.

22. A testing device according to claim 1 wherein said closure mechanism comprises a shutter.

23. A testing device according to claim 1 wherein said tubular body is flexible, and further wherein said closure mechanism comprises adhesive on said tubular body, whereby said tubular body is collapsible and said adhesive is adapted to hold said tubular body in a collapsed condition.

24. A testing device according to claim 1 wherein said closure mechanism comprises a "zip lock" configuration.

25. A testing device according to claim 1 wherein said pressure monitor is disposed on an inner surface of said tubular body.

26. A testing device according to claim 1 wherein said pressure monitor comprises a valve.

27. A testing device according to claim 26 wherein said valve comprises a flap valve.

28. A testing device according to claim 27 wherein said flap valve in said tubular body is a punched or laser cut flap valve.

29. A testing device according to claim 27 wherein said flap valve comprises two conductive trace elements and a circuit therebetween such that (i) when said flap valve is closed, said circuit is open, and (ii) when said flap valve is open, said circuit is closed.

30. A testing device according to claim 1 wherein the pre-determined pressure is 40 mm HG.

31. A testing device according to claim 1 wherein said pressure monitor comprises a strain-sensitive printed resistive element.

32. A testing device according to claim 31 wherein said strain-sensitive printed resistive element is deformable.

33. A testing device according to claim 31 wherein said strain-sensitive printed resistive element (i) is in the first configuration when the pre-determined pressure is not established in the passageway, and (ii) is in the second configuration when the pre-determined pressure is established in the passageway.

34. A testing device according to claim 1 wherein said pressure monitor is formed as part of said tubular body.

35. A testing device according to claim 1 wherein said pressure monitor comprises a sound creation element.

36. A testing device according to claim 1 wherein the output of said pressure monitor is recordable.

37. A method for testing breathing effort of a person, the method comprising the steps of:
providing a testing device comprising a tubular body having a distal end and a proximal end, and a single passageway defined thereby and extending therethrough, an ECG electrode disposed on an exterior surface of the tubular body and engageable by fingers of the person, a breathing flow sensor disposed in the tubular body, a closure mechanism adapted for restricting and closing the passageway, and for rendering the passageway unrestricted, and a pressure monitor mounted within the tubular body for measuring pressure in the passageway;
setting the closure mechanism to provide a selected one of no restriction and a selected degree of restriction of the passageway;
placing fingertips of the person on the ECG electrode;
breathing by the person into the proximal end of the passageway;
measuring the person's inspiration and expiration by the breathing flow sensor;
sensing the person's ECG with the ECG electrode; and
performing at least one of (1) a metronomic breathing test, (2) a Valsalva maneuver, and (3) an HRV test.

* * * * *